United States Patent [19]

Connolly et al.

[11] Patent Number: 5,238,923
[45] Date of Patent: Aug. 24, 1993

[54] AMINO-SUBSTITUTED HETEROCYCLES AS RENIN INHIBITORS

[75] Inventors: Cleo Connolly, Livonia; Annette M. Doherty, Ann Arbor; Harriet W. Hamilton; William C. Patt, both of Chelsea; Ila Sircar, Ann Arbor, all of Mich.

[73] Assignee: Warner-Lambert Company, Ann Arbor, Mich.

[21] Appl. No.: 511,271

[22] Filed: Apr. 25, 1990

Related U.S. Application Data

[63] Continuation-in-part of Ser. No. 357,561, May 26, 1989, abandoned.

[51] Int. Cl.$^5$ ............... A61K 37/02; A61K 31/41; C07K 5/06; C07D 233/66
[52] U.S. Cl. ........................... 514/19; 514/18; 514/359; 530/331; 548/331.5; 548/314.7; 548/312.4
[58] Field of Search ............. 514/19, 18, 359; 530/331; 548/344

[56] References Cited

U.S. PATENT DOCUMENTS

| | | | |
|---|---|---|---|
| 4,839,357 | 6/1989 | Patchett et al. | 514/235.8 |
| 4,845,079 | 7/1989 | Luly et al. | 514/18 |
| 5,036,053 | 7/1991 | Himmelsbach et al. | 514/19 |
| 5,063,207 | 11/1991 | Doherty et al. | 514/18 |

FOREIGN PATENT DOCUMENTS 192554 2/1986 European Pat. Off. .
WO8702675 7/1987 PCT Int'l Appl. .

OTHER PUBLICATIONS

R. Berkow, editor, *The Merck Manual*, 14th Edition, 1982, pp. 2005–2011.
A. Burger, editor, *Medicinal Chemistry*, 2nd Edition, 1960, pp. 565–571, 578–581, 600–601.
J. Plattner, et al., *J. Med. Chem.* 31: 2277–2288 (1988).
E. Haber et al., *J. of Cardiovascular Pharmacology* 10 (*Suppl. 7*): 554–558, 1987.
J. Med. Chem., vol. 30, 1987 pp. 1224–1228.

*Primary Examiner*—Robert A. Wax
*Assistant Examiner*—Stephen Walsh
*Attorney, Agent, or Firm*—Elizabeth M. Anderson

[57] ABSTRACT

The invention concerns novel renin-inhibitory compounds which contain an amino-substituted heterocycle at the $P_2$ position. These are useful for treating renin-associated hypertension, congestive heart failure, glaucoma, hyperaldosteronism, and diseases caused by retroviruses including HTLV-I and -III. Processes for preparing the compounds, compositions containing them, and methods of using them are included. Also included is a diagnostic method which uses the compounds to determine the presence of renin-associated hypertension, or hyperaldosteronism.

4 Claims, No Drawings

AMINO-SUBSTITUTED HETEROCYCLES AS RENIN INHIBITORS

This is a continuation-in-part of U.S. application Ser. No. 07/357,561 filed May 26, 1989, now abandoned.

BACKGROUND OF THE INVENTION

Renin is a natural enzyme which is released into the blood from the kidney. It cleaves its natural substrate, angiotensinogen, releasing decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renin have been sought as agents for control of hypertension, congestive heart failure, and hyperaldosteronism.

European Application Number EP-229667 covers renin inhibiting peptidyl-amino-diols of formula

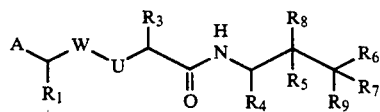

wherein A is a substituent; W is C=O or CHOH; U is $CH_2$ or $NR_2$; $R_1$ is lower alkyl, cycloalkylmethyl, benzyl, 4-methoxybenzyl, halobenzyl, (1-naphthyl)methyl, (2-naphthyl)methyl, (4-imidazoyl)methyl, α,α-dimethylbenzyl, 1-benzyloxyethyl, phenethyl, phenoxy, thiophenoxy or anilino; $R_3$ is lower alkyl, [(alkoxy)alkoxy]alkyl, (thioalkoxy)alkyl, lower alkenyl, benzyl or heterocyclic ring substituted methyl; $R_4$ is lower alkyl, cycloalkylmethyl or benzyl; $R_5$ is vinyl, formyl, hydroxymethyl or hydrogen; $R_7$ is hydrogen or lower alkyl; $R_8$ and $R_9$ are independently selected from OH and $NH_2$; and $R_6$ is hydrogen, lower alkyl, vinyl or arylalkyl.

European Application 186,977 covers certain renin-inhibitory peptides of formula

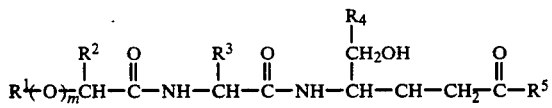

wherein m is 0 or 1 and $R^1$ to $R_3$ are a variety of organic groups. The $R^3$ covers many groups.

Structurally the positions of the various amino acids (amino acid mimics) of the compounds of the instant invention may be designated by reference to the octapeptide which is the minimal angiotensinogen sequence cleaved by renin, namely:

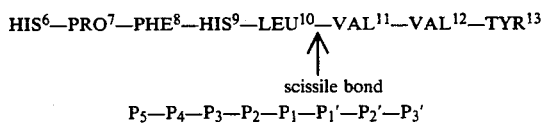

A designation for the compounds of this invention is illustrated below. The CAD is considered to occupy the $P_1$-$P_1'$ positions. For example

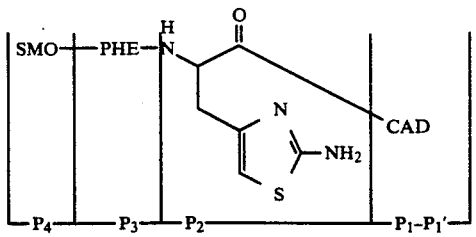

The present invention concerns novel compounds which inhibit renin. It also concerns pharmaceutical compositions containing these novel peptides, methods of treating renin-associated hypertension, congestive heart failure, glaucoma, and hyperaldosteronism, as well as the use of the compounds as diagnostic tools, and the methods for preparing the compounds.

Since HIV protease, like renin, is an aspartyl protease, these compounds can also be used to treat diseases caused by retroviruses including HTLV-I and -III.

SUMMARY OF THE INVENTION

The present invention relates to novel compounds of the formula

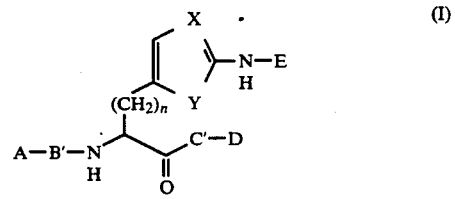

and the pharmaceutically acceptable acid addition salts thereof wherein A, B', C', D, E, n, X, and Y are as defined herein below.

The invention also includes pharmaceutical compositions comprising an effective amount of the above compound of formula I in admixture with a pharmaceutically acceptable carrier or excipient and a method for treating renin-associated hypertension in a patient suffering therefrom comprising administering to said patient the above pharmaceutical composition in unit dosage form.

Further the invention includes a pharmaceutical composition comprising an effective amount of a compound of formula I above in admixture with a pharmaceutically acceptable carrier or excipient, and a method for treating hyperaldosteronism in a patient suffering therefrom comprising administering to said patient the above pharmaceutical composition in unit dosage form.

Further the invention includes a pharmaceutical composition comprising an effective amount of a compound of formula I in admixture with a pharmaceutically acceptable carrier or excipient, and a method for treating congestive heart failure in a patient suffering therefrom comprising administering to said patient the above pharmaceutical composition in unit dosage form.

The present invention also includes the use of compounds of formula I to treat diseases caused by retroviruses.

The present invention also includes the use of compounds of formula I above as diagnostic tools for the identification of cases of hypertension due to renin excess.

The present invention further includes a pharmaceutical composition comprising an amount effective for treating glaucoma. Of a compound of Formula I in admixture with a pharmaceutically acceptable carrier or excipient and a method for treating glaucoma in a patient suffering therefrom comprising administering to said patient the above pharmaceutical composition in unit dosage form.

The invention further includes methods for preparing compounds of formula I above.

DETAILED DESCRIPTION

The following table provides a dictionary of the terms used in the description of the invention.

TABLE I

| Abbreviated Designation | Amino Acid |
|---|---|
| GLU | L-Glutamic Acid |
| ASP | L-Aspartic Acid |
| PHE | L-Phenylalanine |
| TYR (OMe) | O-Methyl-L-tyrosine |
| TYR | L-Tyrosine |
| HIS | L-Histidine |
| ATG | 2-(2'-Amino-4'-thiazolyl)-glycine |
| ATM | 3-(2'-Amino-4'-thiazolyl)-alanine |
| ATE | 4-(2'-Amino-4'-imidazolyl)-ethylglycine |
| AHM | 3-(2'-Amino-4'-imidazoyl)-alanine |
| AHY | 4-(2'-Amino-4'-imidazoyl)-ethylglycine |

C-Terminal Group

CAD

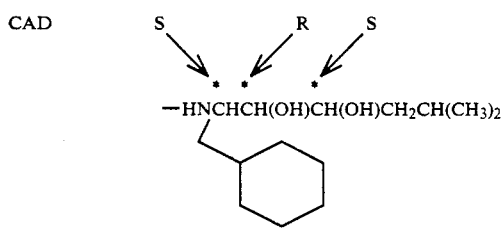

CST $$-HNCHCH(OH)CH_2\overset{O}{\underset{\|}{C}}-$$

(with cyclohexyl-thiazolidine substituent)

STA $$-HNCHCH(OH)CH_2\overset{O}{\underset{\|}{C}}-$$

(with cyclohexylmethyl substituent)

CDH

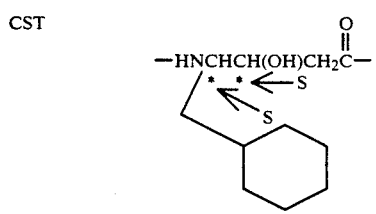

TABLE I-continued

| Abbreviated Designation | Amino Acid |
|---|---|

FCO $$-HNCHCOCF_2\overset{O}{\underset{\|}{C}}-$$

(with cyclohexylmethyl-thio substituent)

FCS $$-HNCHCH(OH)CF_2\overset{O}{\underset{\|}{C}}- \;\; (R, S, RS)$$

(with cyclohexylmethyl-thio substituent)

Miscellaneous Groups

| Z | Benzyloxycarbonyl |
| BOC | Tert-butyloxycarbonyl |
| AC | Acetyl |
| CHO | Formyl |
| TROC | Cl₃CCH₂OCO— |

Miscellaneous Groups

| BBSP | 2-Benzyl-3-(t-butylsulfonyl)propionyl |
| OBZL | Benzyl ester |

MPS

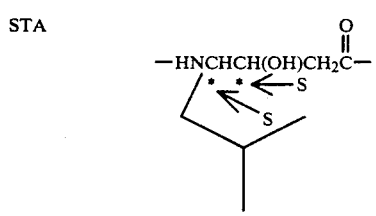

SMO (morpholine-N-sulfonyl group)

DMSA $$Me_2N\overset{O}{\underset{\|}{S}}\overset{\|}{\underset{O}{-}}$$

SPI (piperazine-N-sulfonyl group)

AEM (morpholine-N-CH₂CH₂NH-)

BHEAEA

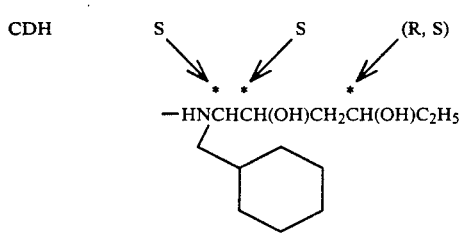

MBA (HN-CH(CH₃)CH₂- type group)

TABLE I-continued

| Abbreviated Designation | Amino Acid |
|---|---|
| PIP | 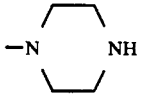 |

| | Solvents and Reagents |
|---|---|
| Et$_2$O | Diethyl ether |
| CHCl$_3$ | Chloroform |
| DMF | N,N-Dimethylformamide |
| DMSO | Dimethylsulfoxide |
| HOBT | Hydroxybenzotriazole |
| DCC | N,N'-Dicyclohexylcarbodiimide |
| HOAc | Acetic acid |
| Et$_3$N | Triethylamine |
| THF | Tetrahydrofuran |
| CH$_2$Cl$_2$ | Dichloromethane |
| MeOH | Methanol |
| EtOAc | Ethyl acetate |
| DMAP | 4-(N,N-Dimethylamino)pyridine |

The compounds of the present invention are represented by the formula

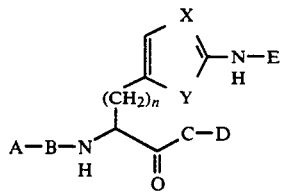

or a pharmaceutically acceptable acid addition salt thereof, wherein

A is H, BOC, BBSP, Z,

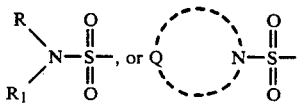

wherein R and R$_1$ are each independently hydrogen or straight or branched chain lower alkyl which is unsubstituted or substituted by one or two hydroxy groups, one or two amino groups or

wherein this is a saturated ring containing two to five carbon atoms wherein Q is CH$_2$, O, S, or NR;

B' is absent, PHE, TYR, or TYR(OMe) with the proviso that when A is BBSP, B' is absent;

C' is CST, FCS, FCO, CAD or STA;

D is absent, OH, NR$_2$R$_3$ wherein R$_2$ and R$_3$ are each independently hydrogen or straight or R$_3$ can also be —(CH$_2$)$_m$X' wherein m is an integer of from zero to eight and X' is —OH,

as defined above, OR$_4$, NR$_5$R$_6$ wherein R$_4$, R$_5$, and R$_6$ are each independently hydrogen, straight or branched chain lower alkyl, substituted or unsubstituted by one or two hydroxy or amino groups with the proviso that when C' is CAD, D is absent;

E is hydrogen, Z, BOC, or lower alkanoyl, n is an integer of from 0 to 2;

X and Y are each independently O, S, N or NH and at least one of X and Y must be N; X and Y cannot both be N.

Preferred compounds of the present invention are those of formula I wherein

A is BOC, BBSP,

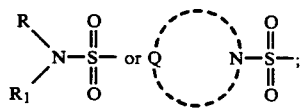

B' is absent, PHE, or TYR(OMe),

C' is CST, FCO, FCS or CAD;

D is absent or

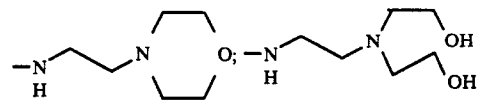

with the proviso that when C is CAD D is absent;

E is hydrogen or lower alkanoyl; and n is one.

More preferred compounds of the present invention are those of formula I wherein

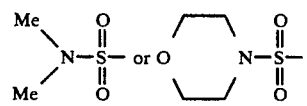

B' PHE or TYR(OMe).

Still more preferred compounds of the present invention are those of formula I wherein A is

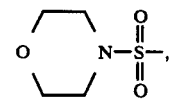

B' is PHE,

C' is CST or CAD, and

E is hydrogen.

Particularly preferred compounds falling within the scope of the invention include the following compounds, their isomers, and pharmaceutically acceptable acid addition salts:

SPI-PHE-ATM(Z)-CAD,
MPS-PHE-ATM(Z)-CAD,
DMSA-PHE-ATM(Z)-CAD,
BBSP-ATM(Z)-CAD,

BBSP-ATM(AC)-CAD,
BBSP-ATM-CST-AEM,
BBSP-ATM-CST-BHEAEA,
SPI-TYR(OME)-ATM(Z)-CAD,
SPI-TYR(OME)-ATM(CHO)-CAD,
BBSP-ATM-FCO-AEM,
DMSA-TYR(OME)-ATM-FCS-AEM,
BOC-PHE-ATM-CAD,
BOC-PHE-ATM-CST-AEM,
BOC-PHE-ATM-CST-BHEAEA,
BBSP-ATG-CAD,
DMSA-PHE-ATG-CST-AEM,
SPI-TYR(OME)-ATG-CAD,
SPI-PHE-ATG-CAD,
SMO-TYR(OME)-ATG-CST-AEM,
SMO-PHE-ATE-CAD,
SMO-TYR(OME)-ATE-CAD,
SMO-PHE-AHM-CAD,
SMO-PHE-AHM-CST-BHEAEA,
DMSA-TYR(OME)-AHY-CST-AEM,
SMO-PHE-ATM-FCS-AEM,
SMO-PHE-ATM-FCO-AEM,
SPI-PHE-ATM-CAD,
BOC-ATG(Z)-FCS-AEM,
ATG(Z)-FCS-AEM,
SMO-PHE-ATG(Z)-FCS-AEM,
SMO-PHE-ATG-FCS-AEM,
SMO-PHE-ATM(TROC)-FCS-OET,
SMO-PHE-ATM(TROC)-FCO-OET,
SMO-PHE-ATM-FCO-OET, and
SMO-PHE-ATG(Z)-FCS-AEM.

Most preferred compounds are:
SMO-PHE-ATM(Z)-CAD,
SMO-PHE-(S)ATM-CAD (Isomer A),
SMO-PHE-ATM-CST-AEM,
SMO-TYR(OME)-ATM-CST-AEM,
SMO-PHE-ATM-CAD (Isomer B),
SMO-TYR(OME)-ATM-CAD,
SMO-PHE-ATG-CAD,
BOC-PHE-ATG-STA-MBA, and
SMO-PHE-ATM-CST-BHEAEA.

The P$_2$ in the present invention may have a substituent (E): E=(Z), (AC) or (CHO), represented by the following abbreviation; ATM(E). The substituent is on the exocyclic nitrogen as shown by

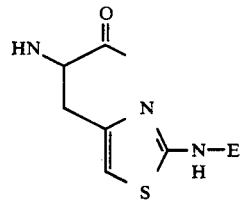

The compounds include solvates and hydrates and pharmaceutically acceptable acid addition salts of the basic compounds of formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic, and the like. The salts are prepared by contacting the free base form with a sufficient amount of the desired acid to produce a salt in the conventional manner. The free base forms may be regenerated by treating the salt form with a base.

The compounds of the present invention possess one or more chiral centers and each center may exist in the R(D) or S(L) configuration. The present invention includes all enantiomeric, epimeric and tautomeric forms as well as the appropriate mixtures thereof.

The S isomer at the P$_2$ position is the more preferred.

Some of the above novel compounds may be prepared in accordance with well-known procedures for preparing compounds from their constituent amino acids. Other of the novel compounds of the present invention are prepared by a step-wise procedure or by a fragment coupling procedure depending upon the particular final product desired.

One process for preparing a compound of formula I comprises:

a) reacting an N-protecting amino acid with a desired amine to produce the corresponding amide, b) deprotecting the N-protecting group of said amide and coupling it with a desired acid to produce a dipeptidyl like amide, and c) further deprotecting the side chain functions on the amide to produce the desired compound of formula I and converting, if desired, to a pharmaceutically salt thereof.

An alternate process for preparing a compound of formula I wherein C' is FCS or FCO comprises:

a) reacting an amino acid ester with TROC protection on the side chain with an N-protected amino acid to produce a dipeptide ester which is then hydrolyzed to the corresponding dipeptide acid, b) coupling the product of step a) with an amine selected from the group consisting of FCS or FCO to produce the TROC-protected compound of claim 1, and c) deprotecting further, if desired, to produce a compound of claim 1 and converting, if desired, to a pharmaceutically acceptable salt thereof.

This is illustrated in Scheme II below.

The following schemes illustrate novel methods of preparing certain compounds of the present invention.

According to Scheme I below, α-BOC,(2'-(Z)-amino-4'-thiazolyl)alanine (1) is reacted with CST-AEM (2) to form an amide (3). The reaction takes place in an inert solvent such as CH$_2$Cl$_2$ or DMF with HOBT and DCC at temperatures of −20° to 30° C. The BOC protecting group of (3) is removed with HCl gas or TFA in an inert solvent such as CH$_2$Cl$_2$ to give the amine (4). This amine (4) is coupled with SMO-PHE (5) in an inert solvent such as CH$_2$Cl$_2$ or DMF with HOBT and DCC at temperatures from −20° to 30° C. to form (6), a compound of the present invention. Furthermore, hydrogenolysis of (6) (removal of Z) by stirring in methanol under a hydrogen atmosphere in the presence of 10-20% palladium on carbon catalyst, with or without the presence of p-toluenesulfonic acid, forms (7) a compound of the present invention.

Scheme I can be modified to include the (TROC) protecting group in place of (Z) in order to improve the synthetic route and provide for the preparation of compounds containing FCO and FCS. The TROC protecting group is useful as it is easier to remove in going from step (6) to (7). The FCO or FCS group is more stable in this situation.

SCHEME I

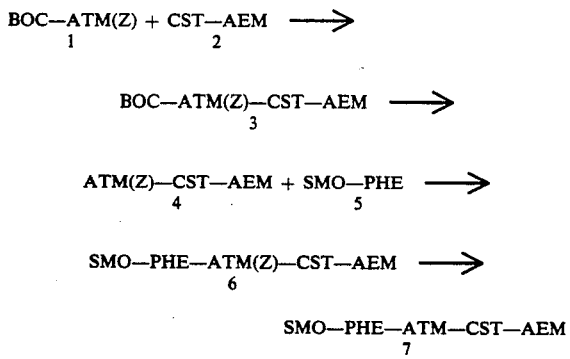

SCHEME II

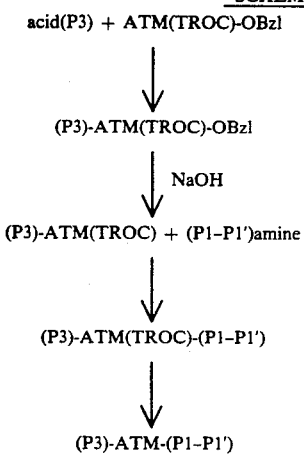

The strategy of peptide chain assembly and selection and removal of protecting groups is discussed in Chapter 1, "The Peptide Bond," in "The Peptides. Analysis, Synthesis, Biology," E. Gross and J. Meienhofer, Eds., Academic Press, New York, N.Y., 1979, Vol. 1, pp. 42-44.

The DCC/HOBT method of coupling is well-known to those skilled in the art and is discussed in Chapter 5, "The Carbodiimide Method" by D. H. Rich and J. Singh in "The Peptides Analysis, Synthesis, Biology," E. Gross and J. Meienhofer, Eds., Academic Press, New York, N.Y., 1979, Vol. 1, pp. 241-261.

Peptide coupling depends on activating the carboxy terminus of the amino protected amino acid and condensing it with another peptide containing a free amino terminus. In addition to the DCC coupling method described above, other methods of activating the carboxyl group of a protected amino acid include:
1) The azide method—described in Chapter 4 of the above reference.
2) The mixed anhydride method—described in Chapter 6 of the above reference.
3) The active ester method—described in Chapter 3 of the above reference.

The term lower alkyl refers to straight or branched chain alkyl radicals containing from one to six carbon atoms including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl, and the like.

The term lower alkanoyl means refers to alkanoyl groups of from one to four carbon atoms.

The compounds of the present invention are useful for treating renin-associated hypertension, congestive heart failure, hyperaldosteronism, and other related illnesses. They are useful as agents in treating glaucoma. They are also useful as diagnostic tools for determining the presence of renin-associated hypertension or hyperaldosteronism.

Pharmaceutical compositions which comprise an effective amount of the compound in combination with a pharmaceutically acceptable carrier are part of the present invention. An important aspect of the present invention is a method of treating renin-associated hypertension in a mammal which comprises administering a pharmaceutical composition containing an effective amount of a compound of the invention in combination with a pharmaceutically acceptable carrier to the mammal.

Another equally important aspect of the present invention is a method of treating hyperaldosteronism in a mammal which comprises administering a pharmaceutical composition containing an effective amount of a compound of the invention in combination with a pharmaceutically acceptable carrier to the mammal.

An additional aspect of the present invention is a method for treating congestive heart failure in a mammal which comprises administering a pharmaceutical composition containing an effective amount of a compound in combination with a pharmaceutically acceptable carrier to the mammal.

Yet another aspect of the present invention is a process for preparing a compound of formula I according to claim 1.

The effectiveness of the aforementioned compounds is determined by a test for in vitro renin inhibitory activity. This activity is determined by a standard radioimmunoassay for angiotensin I. In this assay the enzyme, renin, incubated for 2 hours at 37° C. in the presence of a substrate, angiotensinogen, generates the product, angiotensin I. Test compounds are added to the incubation mixture. Relative activity is r reported as the $IC_{50}$, which is the molar concentration of test compound causing a 50% inhibition of the renin activity.

The compounds of the present invention have the advantages of increased stability toward chymotrypsin hydrolysis, which is described by J Med Chem, Vol. 31, No. 2, page 292, 1988. This property makes the compounds more stable in vivo and therefore they exhibit a longer duration of in vivo activity.

Compounds of this invention have also demonstrated in vivo activity represented by lowering blood pressure in conscious monkeys. In vivo effectiveness is determined by their effect on blood pressure in unanesthetized, sodium-deplete, normotensive Rhesus or Cynomolgus monkeys.

The following describes this test. Monkeys were acclimated to a low sodium diet and trained to rest quietly in a restraining device. Next, vascular access ports were surgically implanted for intravenous administration of test compounds and direct measurement of blood pressure. At least one week was allowed for recovery from surgery before sodium depletion was accomplished by giving furosemide (1 mg/kg/day, IM) for 4 consecutive days. On the seventh day animals were removed from their home cage and placed in the restraining device. After a 20- to 30-minute acclimation period, a control blood sample (arterial) was taken for determination of plasma renin activity (PRA). Next, either vehicle (absolute ethanol, 0.2 mL/kg) or test compound (5 mg/kg) was infused intravenously over a 10-minute period.

Blood pressure was monitored continuously throughout the entire pre- and post-dose period. Blood samples were taken at the mid-point of the infusion and at 0, 15, 30, and 60 minutes post infusion.

The compounds of the present invention also possess the advantage of increased selectivity toward the renin enzyme versus other aspartyl protease enzymes.

TABLE II

In Vitro Renin Inhibition

| Compound | IC$_{50}$ (nM, or % inhibition at concentration) |
|---|---|
| SMO—PHE—ATM—CAD (Isomer A) | 0.38 |
| SMO—PHE—ATM—CAD (Isomer B) (impure sample) | 0.76 |
| SMO—PHE—ATM(Z)—CAD | 0% at $10^{-8}$ |
| BOC—PHE—ATM—CST—AEM | 15% at $10^{-8}$ |
| SMO—PHE—ATM—STA—MBA | 480 |
| BOC—PHE—ATG—STA—MBA | 44% at $10^{-6}$ |
| SMO—PHE—ATM—CST—AEM (Isomer A) | 49.9% at $10^{-6}$ |
| SMO—PHE—ATM—CST—AEM (Isomer B) | 3.4 |
| SMO—TYR(OME)—ATM—CAD (Isomer A) | 0.34 |
| SMO—TYR(OME)—ATM—CAD (Isomer B) | 66 |
| SMO—PHE—ATM(Z)—CST—AEM (Isomer A) | 11.4% at $10^{-8}$ |
| SMO—PHE—ATM(Z)—CST—AEM (Isomer B) | 25.5% at $10^{-8}$ |
| SMO—PHE—ATG—CAD | 0.58 |
| SMO—PHE—ATM(Z)—FCS—AEM | 164 |
| SMO—PHE—ATM—FCS—AEM | 0.58 |
| SMO—PHE—ATM—CDH | 0.27 |
| SMO—PHE—ATE—CAD | 15.3 |
| SMO—PHE—ATE(Z)—CAD | no activity at $10^{-8}$ |
| SMO—PHE—ATG(Z)—FCS—AEM | no activity at $10^{-8}$ |
| SMO—PHE—ATM—FCO—AEM | |
| SMO—PHE—ATM—CST—BHEAEA | 3.6 |
| SPI—PHE—ATM—CAD | 0.16 |

TABLE III

In Vitro Chymotrypsin Stability

| | Percent Parent Remaining (3 hrs) | |
|---|---|---|
| | Buffer only | Buffer + chymotrypsin |
| SMO—PHE—(S)ATM—CAD | 100 | 100 |
| SMO—TYR(OME)—ATM—CAD (Isomer A) | 100 | 100 |

TABLE IV

In Vivo Blood Pressure Lowering by Renin Inhibitors SMO—PHE—(S)ATM—CAD

| | | (mm Hg drop in mean B.P.) | | | | |
|---|---|---|---|---|---|---|
| PO Dose | n at | 1 hr | 2 hr | 4 hr | 6 hr | Max |
| 10 mg/kg | 4 | 14 | 20 | 15 | 12 | 23 |
| 30 mg/kg | 6 | 30 | 34 | 29 | 29 | 38 |

As can be seen from the above tables, the compounds of the present invention have a significant effect on the activity of renin and thus are useful for the treatment of hypertension, hyperaldosteronism, and congestive heart failure.

The compounds of the instant invention, when tested by measuring the effect on intraocular pressure in rabbits as described by Tinjum, A. M., *Acta Ophthalmologica* 50, 677 (1972), are expected to exhibit antiglaucoma activity.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be encapsulating material. In powders, the carrier is a finely divided solid which is in admixture with the finely divided compound. In the tablet the active compound is mixed with carrier having the necessary binding properties in suitable proportions and compacted in the shape and size desired. The powder and tablets preferably contain from 5 to 10 to about 70 percent of the active ingredient. Suitable solid carriers are magnesium carbonate, magnesium stearate, talc, sugar, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compound of the present invention may be administered orally, buccally, parenterally, by inhalation spray, rectally, or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection, or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions These particular solid form preparations are most conveniently provided in unit dosage form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70-kg subject is from 1 to 2500 mg per day or preferably 25 to 750 mg per day optionally in divided portions. The dosages, however, per day may be varied depending upon the requirements of the patient, the severity of the condition being treated, and the compound being employed. Determination of the proper dosage for a particular situation is within the skill of the art. Generally, treatment is initiated with small dosages which are less than the optimum dose of the compound. Thereafter the dosage is increased by small increments until the optimum effect under the circumstances is reached. For convenience, the total daily dosage may be divided and administered in portions during the day if desired.

In therapeutic use as an antiglaucoma agent, the compound may also be administered as a topical corneal application of a solution containing the compound in amounts as known to one skilled in the treatment.

The present invention includes combinations of novel renin-inhibiting compounds of formula I with one or more antihypertensive agents selected from the group consisting of diuretics, α- and/or β-adrenergic blocking agents, calcium channel blocking agents, central nervous system-acting agents, adrenergic neuron blocking agents, vasodilators, angiotensin converting enzyme inhibitors, and other antihypertensive agents.

The following examples are provided to enable one skilled in the art to practice the present invention. These examples are not intended in any way to limit the scope of the invention but are illustrative thereof.

EXAMPLE 1

SMO-PHE-ATM(Z)-CAD

A mixture of SMO-PHE (0.786 g), HOBT (0.339 g), and DCC (0.516 g) was stirred at 0° C. and treated with ATM(Z)-CAD (1.4 g). The mixture was warmed to room temperature and stirred overnight. The reaction mixture was filtered free of precipitate and the filtrate evaporated in vacuo. The residue was dissolved in ethyl acetate (100 mL) and washed successively with 1M citric acid (100 mL), saturated $NaHCO_3$ (100 mL) and saturated salt solution (100 mL). The organics were dried over $MgSO_4$ and evaporated in vacuo to give a yellow foam. The foam was chromatographed over silica gel to give 1.5 g of the product as a mixture of two diastereomers; mp 95–97° C.

Analyzed for $C_{41}H_{58}N_6O_9S_2.0.5$ $CHCl_3$:
Calc'd: C, 55.82; H, 6.61; N, 9.43.
Found: C, 56.06; H, 6,68; N, 9.15.
The structure was confirmed by NMR and mass spectroscopy.

EXAMPLE 2

SMO-TYR(OME)-ATM(Z)-CAD

The product was synthesized as in Example 1, from SMO-TYR(OME) (0.860 g), HOBT (0.338 g), DCC (0.516 g), and ATM(Z)-CAD (1.4 g). This gave 1.3 g of the product as a mixture of diastereomers, mp 101–107° C.

Analyzed for $C_{42}H_{56}N_6O_9S_2.0.5$ ether:
Calc'd: C, 58.06; H, 7.21; N, 9.23.
Found: C, 58.39; H, 6.93, N, 9.05.
The structure was confirmed by NMR and mass spectroscopy.

EXAMPLE 3

BOC-PHE-ATM(Z)-CST-AEM

The product was synthesized as in Example 1 from BOC-PHE (0.451 g), HOBT (0.230 g), DCC (0.351 g), and ATM(Z)-CST-AEM (1.2 g). This gave 1.2 g of product. This material was used to prepare the product of Example 4. The structure was confirmed by NMR and mass spectroscopy.

EXAMPLE 4

BOC-PHE-ATM-CST-AEM

BOC-PHE-ATM(Z)-CST-AEM (1.05 g) was slurried with 20% Pd/C (0.3 g) and p-toluenesulfonic acid (0.476 g) in methanol (25 mL) under a hydrogen atmosphere. The mixture was stirred for 2 hours, filtered free of catalyst, and evaporated in vacuo. The residue was dissolved in ethyl acetate (75 mL). The organic phase was washed with sodium carbonate (75 mL) and sodium chloride (50 mL), then dried over $MgSO_4$ and evaporated in vacuo. The residue was co-evaporated once with methanol (10 mL) to give 0.63 g of the product as a white foam as a mixture of diastereomers, mp 95–103° C.

Analyzed for $C_{37}H_{57}N_7O_7S.0.9$ MeOH:
Calc'd: C, 58.90; H, 7.90; N, 12.69.
Found: C, 59.15; H, 8.05; N, 12.37.
The structure was confirmed by NMR and mass spectroscopy.

EXAMPLES 5 AND 6

SMO-PHE-ATM(Z)-CST-AEM

Isomer A (5) and Isomer B (6)

The product was synthesized as in Example 1 from SMO-PHE (0.817 g), HOBT (0.351 g), DCC (0.536 g), and ATM(Z)-CST-AEM (1.7 g). This gave 2.0 g of product as a mixture of diastereomers which were separated by chromatography over silica gel. The fast eluting isomer is Isomer A.

Isomer A (5) (0.64 g), mp 102–110° C.
Analyzed for $C_{44}H_{62}N_8O_{10}S_2.0.4$ $CHCl_3$:
Calc'd: C, 54.70; H, 6.45; N, 11.49.
Found: C, 54.66; H, 6.64; N, 11.37.
Isomer B (6) (0.63 g), mp 105–110° C.
Analyzed for $C_{44}H_{62}N_8O_{10}S_2.0.4$ $CHCl_3$):
Calc'd: C, 54.70; H, 6.45; N, 11.49.
Found: C, 54.46; H, 6.58; N, 11.56.

Both isomers show consistent NMR and mass spectra.

EXAMPLE 7

SMO-PHE-ATM-CST-AEM (Isomer A)

The product was synthesized as in Example 4 from SMO-PHE-ATM(Z)-CST-AEM (Isomer A) (0.717 g), p-toluenesulfonic acid (0.366 g) and 20% Pd/C (0.3 g). This gave 0.427 g of product as a white solid, mp 109–119° C.

Analyzed for $C_{26}H_{56}N_8O_8S_2$:
Calc'd: C, 53.80; H, 7.35; N, 13.53.
Found: C, 53.70; H, 7.33; N, 13.48.

The structure was confirmed by NMR and mass spectroscopy

EXAMPLE 8

SMO-PHE-ATM-CST-AEM (Isomer B)

The product was synthesized as in Example 4 from SMO-PHE-ATM(Z)-CST-AEM (Isomer B) (0.883 g), p-toluenesulfonic acid (0.453 g) and 20% Pd/C (0.4 g). This gave 0.544 g of product as a white foam, mp 100–113° C.

Analyzed for $C_{36}H_{56}N_8O_8S_2.1.3$ MeOH:
Calc'd: C, 53.67; H, 7.39; N, 13.43.
Found: C, 54.01; H, 7.40; N, 13.19.

The structure was confirmed by NMR and mass spectroscopy.

EXAMPLES 9 AND 10

Isomer A, fast eluting (9);

Isomer B, slow eluting (10)

The product was synthesized as in Example 4 from SMO-PHE-ATM(Z)-CAD (4.8 g), p-toluenesulfonic acid (2.182 g), and 20% Pd/C (0.4 g). This gave 0.91 g of a mixture of diastereomers as a white foam, which were separated by chromatography over silica gel.

Isomer A (1.50 g), mp 104–112° C.
Analyzed for $C_{33}H_{52}N_6O_7S_2.0.1CH_2Cl_2.0.4$ EtOAc:
Calc'd: C, 55.37: H, 7.42; N, 11.17.
Found: C, 55.40; H, 7.28; N, 10.94.
Isomer B (1.30 g), mp 109–122° C.
Analyzed for $C_{33}H_{52}N_6O_7S_2.0.1CH_2Cl_2.0.4$ EtOAc:
Calc'd: C, 55.37; H, 7.42; N, 11.17.
Found: C, 55.09; H, 7.25; N, 10.86.

Both isomers showed consistent NMR and mass spectra.

EXAMPLE 9 Method B

SMO-PHE-ATM-CAD, Isomer A or SMO-PHE-(S)ATM-CAD

The product was synthesized as in Example 1 from SMO-PHE (0.628 g), Et,N: (0.505 g), HOB7 (0.270 g), DCC (0.413 g) and (S)-ATM-CAD.2HCl (1.1 g). The crude product was chromatographed over silica gel to give 0.375 g of the pure compound as a single diastereomer, mp 106°–113° C.

Analyzed for $C_{33}H_{52}N_6O_7S_2.0.3$ EtOAc:
Calc'd: C, 55.86; H, 7.46; N, 11.43.
Found: C, 55.51; H, 7.50; N, 11.37.

The compound showed Consistent NMR and mass spectra.

EXAMPLE 9 Method C

SMO-PHE-(S)ATM-CAD

A solution of 10.60 g SMO-PHE-(S)ATM(TROC)-CAD (12.0 mmol) was dissolved in 250 mL 4:1, THF (freshly distilled)/MeOH, in a 500 mL roundbottom flask at room temperature under a nitrogen atmosphere. To this was added 6.41 g ammonium chloride 10 equivalents, and 1.57 g zinc dust, 2 equivalents. The reaction was stirred vigorously at ambient temperature. After 2 hours another two equivalents of zinc was added. After another 2 hours, another 2 equivalents for a total of 6 equivalents zinc. After 5.5 hours the reaction mixture was filtered and concentrated to afford 10.96 g white foam. The reaction mixture was chromatographed ($SiO_2$, 1:1 ethyl acetate/$CH_2$). A solid of 1.02 g was filtered from the sample prior to introduction onto the column. Product of 6.47 g was isolated. Mass spectrum m/e=709.2.

EXAMPLES 11 AND 12

SMO-TYR(OME)-ATM-CAD

Isomer A, fast eluting (11);

Isomer B, slow eluting (12)

The product was synthesized as in Example 4 from SMO-TYR(OME)-ATM(Z)-CAD (1.4 g), p-toluenesulfonic acid (0.610 g) and 20% Pd/C (0.25 g). This gave 1.1 g of a mixture of diastereomers as a white foam. The isomers were separated by chromatography over silica gel.

Isomer A (0.330 g), mp 110–120° C.
Analyzed for $C_{34}H_{54}N_6O_8S_2.MeOH.H_2O$:
Calc'd: C, 53.28; H, 7.66; N, 10.65.
Found: C, 53.39; H, 7.23; N, 10.41.
Isomer B (0.240 g), mp 106–116° C.
Analyzed for $C_{34}H_{54}N_6O_8S_7.1.5MeOH$:
Calc'd: C, 54.17; H, 7.68; N, 10.68.
Found: C, 54.24; H, 7.36; N, 10.67.

Both isomers showed consistent NMR and mass spectra.

EXAMPLE 13

SMO-PHE-ATM(Z)-STA-MBA

The product was formed as in Example 1 from SMO-PHE(0.517 g), HOBT (0.222 g), DCC (0.339 g), and ATM(Z)-STA-MBA (0.90 g). This gave 1.1 g of product as a mixture of diastereomers as a white foam, mp 97–103° C.

Analyzed for $C_{40}H_{57}N_7O_9S_2.1.5MeOH$:
Calc'd: C, 55.87; H, 7.11; N, 10.99.
Found: C, 55.51; H, 6.71; N, 10.83.

The structure was confirmed by NMR and mass spectroscopy.

EXAMPLE 14

SMO-PHE-ATM-STA-MBA

The product was synthesized as in Example 4 from SMO-PHE-ATM(Z)-STA-MBA (1.0 g), p-toluenesulfonic acid (0.228 g) and 20% Pd/C (0.3 g). This gave 0.399 g of product as a mixture of diastereomers, mp 97–108° C.

Analyzed for $C_{32}H_{51}N_7O_7S_2 \cdot 0.65Et_2O$:
Calc'd: C, 54.82; H, 7.65; N, 12.94.
Found: C, 54.73 H, 7.57; N, 12.97.

The structure was confirmed by NMR and mass spectroscopy.

EXAMPLE 15

BOC-PHE-ATG(Z)-STA-MBA

The product was synthesized as in Example 1 from ATG(Z)-STA-MBA (1.6 g), HOBT (0.419 g), DCC (0.640 g), and BOC-PHE (0.796 g). This gave 1.6 g of product as a mixture of diastereomers as a light yellow foam, mp 108–118° C.

Analyzed for $C_{40}H_{56}N_6O_8S$ (99%):
Calc'd: C, 60.89; H, 7.16; N, 10.65.
Found: C, 60.98; H, 7.19; N, 10.55.

The structure was confirmed by NMR and mass spectroscopy.

EXAMPLE 16

BOC-PHE-ATG-STA-MBA

The product was synthesized as in Example 4 from BOC-PHE-ATG(Z)-STA-MBA (1.5 g), p-toluenesulfonic acid (0.38 g) and 10% Pd/C. This gave 0.31 g of product as a mixture of diastereomers as a white solid, mp 174–176° C.

Analyzed for $C_{32}H_{50}N_6O_6S$ (99%):
Calc'd: C, 59.79; H, 7.72; N, 12.87.
Found: C, 59.97; H, 7.99; N, 13.06.

The structure was confirmed by NMR and mass spectroscopy.

EXAMPLE 17

TROC-SPI-PHE-(S)ATM(TROC)-CAD

A solution of 2.10 g (TROC) SPI-PHE (4.30 mmol) in 30 mL DMF was treated with 0.89 g DCC (4.30 mmol) and 0.58 g HOBT (4.30 mmol). The materials were allowed to stir at 15° C. for 30 minutes. Then 2.50 g of (S)ATM(TROC)-CAD (4.25 mmol) in 10 mL MDF was added and the ice bath removed. The mixture continued stirring at RT for 48 hours. The reaction mixture was filtered and evaporated in vacuo. The residue was taken up in $CH_2Cl_2$ and washed with 5% $Na_2CO_3$ and saturated NaCl. The organic layer was dried over $MgSO_4$ and evaporated. Chromatography on silica gel eluting with a gradient of straight $CHCl_3$ to 2% MeOH in $CHCl_3$ gave 3.95 g of product. Structure was confirmed by NMR spectroscopy.

EXAMPLE 18

SPI-PHE-(S)ATM-CAD

A solution of 2.00 g TROC-SPI-PHE-(S)ATM-(TROC)-CAD (1.89 mmol) in a 1:1 mixture of 40 mL HOAc:MeOH was treated with 3.50 g zinc dust. These materials were sonicated at ambient bath temperature under $N_2$ atmosphere for 7 hours. The reaction mixture was diluted with $Et_2O$, filtered, and evaporated. The residue was taken up in EtOAc and washed twice with saturated $NaHCO_3$. The organic layer was dried over $MgSO_4$, and evaporated. Chromatography on silica gel eluting with a gradient 2 to 8% MeOH in $CHCl_3$ gave 0.47 g of the product. The structure was confirmed by NMR and mass spectroscopy.

Analyzed for for $C_{33}H_{53}N_7S_2O_6 \cdot 1.0$ $CH_2Cl_2$ (MW 792.89):
Calc'd: C, 51.54; H, 6.99; N, 12.37.
Found: C, 51.21; H, 6.77; N, 12.26.

EXAMPLE 19

SMO-PHE-(S)ATM(TROC)-CDH

A solution of 0.89 g (BOC)-(S)ATM(TROC)-CDH was dissolved in $CH_2Cl_2$ and cooled in an ice bath. HCl was bubbled through for 10 minutes, and the reaction stirred an additional 30 minutes, then concentrated to give 0.91 g off-white foam. This was redissolved in $CH_2Cl_2$ and cooled, and 0.42 g SMO-PHE, 0.27 g DCC, 0.18 g HOBT, and 0.48 g DMAP added. After coming to ambient temperature overnight, the reaction mixture was filtered and washed sequentially with 5% citric acid, saturated $NaHCO_3$, and saturated NaCl, then concentrated. The 1.12 g solid was chromatographed ($SiO_2$, EtOAc), and 0.71 g product collected. Mass spectrum m/e=872.

EXAMPLE 20

SMO-PHE-(S)ATM-CDH

A compound of 0.68 SMO-PHE-(S)ATM(TROC)-CDH was dissolved in 4:1 THF/MeOH. Ammonium chloride of 0.35 g and 0.10 g zinc dust were added and the reaction stirred at room temperature. After 1 hour another 0.10 g zinc was added, and another 0.10 g zinc after 2 hours. After 5 hours the reaction mixture was filtered and concentrated. The residue was dissolved in methanol and 10 mL HOAc added, along with 0.30 g zinc. The reaction was heated; after 45 minutes another 0.30 g zinc and reaction stirred for an hour. After cooling the mixture was filtered, diluted with $Et_2O$, and poured in $NaHCO_3$ solution. The layers were separated, the aqueous washed with more ether, and the combined organics concentrated to give ca. 1.3 g glass. This acid sequence was repeated, and worked up by concentration of the filtrate, dissolving in EtOAc and a $NaHCO^3$ wash. Concentration of the organics gave 0.41 g solid which was chromatographed ($SiO_2$, 95% $CHCl_3$ 5% MeOH). Product of 0.32 g was obtained. Mass spectrum m/e=695.

EXAMPLE 21

SMO-PHE-(S)ATM(TROC)-CAD

A solution of 32.93 g (BOC)-(S)ATM(TROC)-CAD (47.8 mmol), milled, was suspended in ether/methanol (300 mL/20 mL) and cooled in ice water bath. HCl was bubbled through for 20 minutes. An initial white precipitate went back into solution during this time. The reaction mixture was stored in the refrigerator overnight. The reaction mixture was concentrated, the foam stirred vigorously with ether and the resulting white solid filtered and dried to afford 27.5 g powder (44.0 mmol, 92% as amine hydrochloride, subsequent calculations based on this). The material was used without further purification. This amine was suspended in 500 mL $CH_2CL_2$, the flask cooled in ice water bath, and 13.83 g SMO-PHE, 5.96 g HOBT, 5.83 g DMAP, and 9.06 g DCC added. The mixture was allowed to come to ambient temperature overnight. It was filtered, and the filtrate washed sequentially with water, 5% aqueous citric acid, saturated $NaHCO_3$, and saturated NaCl, then dried over $Na_2SO_4$ and concentrated to give 31.23 g white foam. This material was chromatographed in two lots (SiO$_2$, eluting with 2:1 ethyl acetate/hexane). Total 11.38 g desired product isolated. Mass spectrum m/e=885.

EXAMPLE 22

SMO-PHE-(S)ATM(TROC)-FCS-AEM

To SMO-PHE (0.87 g, 2.46 mmol) and HOBt (0.37 g, 2.76 mmol) in anhydrous DMF (20 mL) at 0° C. was added DCC (0.57 g, 2.76 mmol) in DMF (5 mL) followed by (S)ATM(TROC)-FCS-AEM (1.95 g, 2.76 mmol) in DMF (5 mL). After stirring for 2 hours, the reaction was allowed to warm to room temperature and stirred for a further 16 hours. The precipitated dicyclohexylurea was removed by filtration and the solvent evaporated under reduced pressure. The crude residue was taken up in ethyl acetate and washed with saturated aqueous sodium bicarbonate followed by brine. After drying (Na$_2$SO$_4$), filtration and evaporation of the solvent the crude product was chromatographed on silica gel eluting with 5% methanol in dichloromethane. The structure of the major product (1.35 g, 49%), obtained as a white foam, was confirmed by NMR and mass spectroscopy; MS (FAB); MH+ 1005.3; (HPLC-98% purity).

Analyzed for C$_{39}$H$_{55}$N$_8$O$_{10}$S$_2$O$_3$F$_2$.0.2CH$_2$Cl$_2$:
Calc'd: C, 46.09: H, 5.42; N, 10.97; S, 6.28.
Found: C, 45.77; H, 5.55: N, 10.82; S, 6.09.

EXAMPLE 23

SMO-PHE-(S)ATM-FCO-AEM

To SMO-PHE-(S)ATM(TROC)-FCS-AEM (1.95 g, 1.94 mmol) in anhydrous CH$_2$Cl$_2$ (40 mL) at 0° C. was added dichloroacetic acid (0.23 mL, 2.91 mmol) followed by DCC (4.02 g, 19.4 mmol) in CH$_2$Cl$_2$ (5 mL) and finally anhydrous DMSO (3.2 mL, 19.4 mmol). After 2 hours at 0° C., the reaction was allowed to warm to room temperature and stirred for a further 16 hours. After recooling to 0° C. a solution of oxalic acid (3.05 g) in methanol (30 mL) was added dropwise to the reaction mixture. After stirring for 20 minutes, the suspension was filtered and evaporated under reduced pressure. The residue was taken up in ethyl acetate and refiltered. After evaporation, this procedure was repeated once more. Evaporation under reduced pressure gave SMO-PHE-(S)ATM(TROC)-FCO-AEM as a viscous yellow oil.

This was dissolved in a mixture of methanol and THF (1:4, 30 mL total). Activated zinc dust (325 mesh) (0.27 g, 3.86 mmol) and excess solid ammonium chloride (2 g) was added and the suspension stirred rapidly for 30 hours. Further zinc dust (0.27 g) was added after 15 hours. Diethyl ether (30 mL) was added and the reaction mixture filtered and evaporated under reduced pressure to give a white foam. The foam was dissolved in a 4:1 mixture of H$_2$O and H$_3$PO$_4$ (200 mL) and washed twice with portions of ethyl acetate (50 mL). The combined organic solution was extracted once with 20% aqueous H$_3$PO$_4$ (100 mL). The combined aqueous extracts were washed once more with ethyl acetate (50 mL) and then cooled to 0° C. and brought to pH 4.5 by careful addition of ammonium hydroxide (followed with pH meter). The solution was then extracted several times with ethyl acetate and dried (Na$_2$SO$_4$). After evaporation under reduced pressure the crude product was obtained as a yellow foam (1.20 g). Column chromatography eluting with 5 to >10% gradient of methanol in ethyl acetate on silica gel gave purified product. Combination of the relevant fractions gave a major diastereoisomer (0.50 g) [indicated by HPLC >95% purity as a 98:2 mix as isomers]. The structure was confirmed by NMR and mass spectroscopy. The compound was converted to the methanesulphonic acid salt:

Analyzed for C$_{36}$H$_{52}$N$_8$O$_8$F$_2$S$_2$ CH$_3$SO$_3$H.3.2 H$_2$O:
Calc'd: C, 45.31; H, 6.41; N, 11.42; S, 9.81.
Found: C, 45.31; H, 6.46; N, 11.18; S, 9.49.
MH+; 827.0.

EXAMPLE 24

SMO-PHE-ATG(Z)-CAD

A solution of 1.41 g (4.4 mmol) of SMO-PHE, 0.53 g (4.4 mmol) of Et$_3$N, 0.62 g (4.4 mmol) of HOBT, and 2.5 g (4.4 mmol) of ATG(Z)-CAD.HCl in a mixture of 40 mL of CH$_2$Cl$_2$ and 5 mL of DMF was cooled in ice and treated with 0.97 g (4.4 mmol) of DCC in 5 mL of CH$_2$Cl$_2$. After 0.5 hours at 0° C., the mixture was allowed to stir at room temperature for 48 hours. The urea was filtered off and the residue was washed with CH$_2$Cl$_2$. The filtrate and the washings were combined, and washed successively with water, saturated NaHCO$_3$, and brine. Drying and removal of the solvent under reduced pressure gave the crude product. This was purified via chromatography (SiO$_2$, CH$_2$Cl$_2$/CH$_3$OH 5%) to give 3.4 g of product. The structure was confirmed by NMR and mass spectroscopy. (M+1 ion peak at 829).

EXAMPLE 25

SMO-PHE-ATG-CAD

A solution of 2 g of SMO-PHE-ATG(Z)-CAD in MeOH (75 mL) containing 0.87 g of p-toluene sulfonic acid and 0.5 g of 20% Pd/C was saturated with hydrogen. Methanol was stripped and the residue was taken up in EtOAc. The solution was washed with NaHCO$_3$, followed by brine, dried and stripped to yield a foam (1.6 g). It was chromatographed (SiO$_2$ 70 g; CH$_2$Cl$_2$/CH$_3$OH 5%) to obtain 1.1 g of the product. Mass spectrum indicate (M+1) ion peak at 695. NMR was consistent with the desired product.

Analyzed for C$_{32}$H$_{50}$N$_6$O$_7$S$_2$.0.5 H$_2$O:
Calc'd: C, 54 60; H, 7.25; N, 11.94.
Found: C, 54.60; H, 7.36; N, 12.17.

EXAMPLE 26

SMO-PHE-(S)ATE(Z)-CAD

BOC-(S)ATE(Z)-CAD (2.38 g) was added to HCl saturated CH$_2$Cl$_2$ at 0° C. and stirred for 1 hour. The reaction mixture was concentrated to 2.3 g pale yellow foam which was used without further purification. The amine hydrochloride was dissolved in CH$_2$Cl$_2$ at 0° C. and to this added 1.13 g SMO-PHE, 0.74 g DCC, 0.49 g HOBT (1 equivalent each) and 1.00 g DMAP (2.27 equivalents). The reaction was allowed to come to ambient temperature overnight, then filtered and washed sequentially with 5% aqueous citric acid, saturated NaHCO$_3$, aqueous saturated NaCl, and dried (MgSO$_4$). After concentration, the residue was chromatographed (SiO$_2$, 95% CHCl$_3$ 5% MeOH) to give 2.27 g of product. Mass spectrum m/e=857

EXAMPLE 27

SMO-PHE-(S)ATE-CAD

SMO-PHE-(S)ATE(Z)-CAD (2.05 g) was dissolved in methanol to which was added 0.40 g 20% Pd/C and 1.18 g tosyl acid. This was put under a hydrogen atmosphere with stirring for 15 hours, then filtered and concentrated to give 1.21 g off-white foam. This was chromatographed (SiO$_2$, EtOAc), and 0.51 g product isolated. Mass spectrum m/e=723.3

EXAMPLE 28

SMO-PHE-(S)ATM(Z)-FCS-AEM

The product was synthesized as in Example 1 from 2.8 g SMO-PHE-(S)ATM(Z), 0.554 g HOBT, 0.846 g DCC, and 1.5 g FCS-AEM. Chromatography (silica gel) with O to >10% MeOH gradient in CH$_2$Cl$_2$ gave 2.0 g product. mp=96-109° C.

Analyzed for C$_{44}$H$_{60}$F$_2$N$_8$O$_{10}$S$_2$.0.9CH$_3$OH:
Calc'd: C, 54.36; H, 6.46; N, 11.30.
Found: C, 54.06; H, 6.38; N, 11.33.

EXAMPLE 29

SMO-PHE-(S)ATM-FCS-AEM

The compound was synthesized as in Example 4 from 1.6 g SMO-PHE-(S)ATM(Z)-FCS-AEM and 0.4 g 20% Pd/C. Silica gel chromatography with a 5 to 10% methanol gradient in CHCl$_3$ gave 0.561 g product. mp=103-115° C.

Analyzed for C$_{36}$H$_{54}$F$_2$N$_8$O$_8$S$_2$.0.6 CHCl$_3$:
Calc'd: C, 48.81; H, 6.11; N, 12.44.
Found: C, 48.74; H, 6.25; N, 12.23.

EXAMPLE 30

SMO-PHE-(S)ATM(Z)-CST-BHEAEA

To BOC-ATM(Z)-CST-BHEAEA (3.2 g) in 60 mL CH$_2$Cl$_2$ and 10 mL of methanol was added HCL (g) for 10 minutes. The solution was evaporated in vacuo to dryness. The residue was dissolved in DMF and treated with diisopropyl ethyl amine until basic to wet litmus. The new solution was treated with SMO-PHE (1.34 g), HOBT (0.61 g), and DCC (0.94 g). The mixture was filtered and evaporated to give 4.61 g crude material. The product was purified by silica gel chromatography. Eluting with 19:1, CH$_2$Cl$_2$:MeOH, gave 1.18 g pure product MS (FAB) M+=945.4. The structure was confirmed by IR, NMR, and mass spectroscopy.

EXAMPLE 31

SMO-PHE-(S)ATM-CST-BHEAEA

The product was prepared as in Example 4 from SMO-PHE-ATM(Z)-CST-BHEAEA (1.06 g), p-TsOH (0.6 g), 20% Pd/C (0.6 g) in MeOH (40 mL). This gave 0.34 g product after silica gel chromatography (19:1, CH$_2$Cl$_2$:MeOH). mp=93-96° C.

Analyzed for C$_{36}$H$_{58}$N$_8$O$_9$S$_2$.0.85CHCl$_3$:
Calc'd: C, 48.50; H, 6.50; N, 12.28.
Found: C, 48.56; H, 6.65; N, 12.07.

The structure was verified by IR, NMR, and mass spectroscopy.

EXAMPLE 32

SMO-PHE-(S)ATM(TROC)-FCS-OET

The compound was synthesized as in Example 1 from SMO-PHE (0.993 g), HOBT (0.43 g), DCC (0.65 g) and (S)ATM(TROC)-FCS-OET (1.97 g). This gave, after silica gel chromatography (6:4, EtOAc:hexane), 1.53 g of product as a white foam. MS, M+=921.

Analysis:
Calc'd: C, 45.68; H, 5.15; N, 9.13.
Found: C, 45.92; H, 5.26; N, 8.99.

NMR and IR spectra were consistent with assigned structures.

EXAMPLE 33

SMO-PHE-(S)ATM(TROC)-FCO-OET

The compound was synthesized as in the first half of Example 23 from SMO-PHE-(S)ATM(TROC)-FCS-OET (1.56 g), DMSO (3.5 mL), dichloroacetic acid (0.073 mL), and DCC (3.65 g). This gave after silica gel chromatography (EtOAc:hexane) 1.4 g of product as a white foam. MS, M+=919. NMR is consistent with proposed structure.

EXAMPLE 34

SMO-PHE-(S)ATM-FCO-OET

The compound was prepared as in the second half of Example 23 from SMO-PHE-(S)ATM(TROC)-FCO-OET (1.32 g), ammonium chloride (0.7 g) and Zn dust (0.4 g). This gave, after silica gel chromatography (EtOAC:hexane (1:1)), 0.7 g of product as a white foam. NMR, IR, and mass spectra all are consistent with the structure.

Analysis:
Calc'd: C, 51.68; H, 5.98; N, 11.30.
Found: C, 51.39; H, 6.05; N, 10.89.

EXAMPLE 35

SMO-PHE-ATG(Z)-FCS-AEM, Isomer A

The compound was synthesized as in Example 1 from SMO-PHE (0.74 g), HOBT (0.32 g), DCC (0.5 g), and ATG(Z)-FCS-AEM, Isomer A (1.5 g). This gave, after silica gel chromatography (3-10% MeOH in 1:1 (EtOAc:CH$_2$Cl$_2$)), 1.26 g of product as a foam. Analyzed for 0.2CH$_2$Cl$_2$:
Calc'd: C, 53.72; H, 6.05; N, 11.49.
Found: C, 53.38; H, 6.03; N, 11.49.

EXAMPLE 36

SMO-PHE-ATG-FCS-AEM, Isomer A

The compound was synthesized as in Example 4 from SMO-PHE-ATG(Z)-FCS-AEM, Isomer A (1.0 g), 20% Pd/C (0.25 g), and p-toluenesulfonic acid hydrate (0.6 g). This gave, after silica gel chromatography (5% MeOH in 1:1 (EtOAc:CH$_2$Cl$_2$)), 0.1 g of product.

Analyzed for .H$_2$O:
Calc'd: C, 50.51; H, 6.50; N, 13.45.
Found: C, 50.46; H, 6.55; N, 12.82.

NMR and IR spectra were consistent with structure. MS, M+=815.

EXAMPLE 37

SMO-PHE-ATG(Z)-FCS-AEM, Isomer B

The compound was synthesized as in Example 1 from SMO-PHE (0.84 g), HOBT (0.36 g), DCC (0.57 g), and ATG(Z)-FCS-AEM, Isomer B (1.7 g). This gave, after silica gel chromatography (3-10% MeOH in 1:1 EtOAc:CH$_2$Cl$_2$), 1.8 g of product as a foam.

Analyzed for 0.2CH$_2$Cl$_2$:
Calc'd: C, 53.72; H, 6.05; N, 11.60.
Found: C, 53.41; H, 6.19; N, 11.32.

NMR and IR were consistent with structure.

EXAMPLE 38

SMO-PHE-ATG-FCS-AEM, Isomer B

The compound was synthesized as in Example 4 from SMO-PHE-ATG(Z)-FCS-AEM, Isomer B (2.5 g), 20% Pd/C (0.5 g) and p-toluenesulfonic acid (1.5 g). This gave, after silica gel chromatography, 1.0 g of the product as a foam.

Analysis:
Calc'd: C, 51.62; H, 6.38; N, 13.76.
Found: C, 51.39; H, 6.56; N, 12.85.
NMR and IR spectra were consistent with the structure.
MS, M+ = 815.

INTERMEDIATES FOR EXAMPLES 1–38

A

DMSA-PHE

A solution of PHE (3.3 g) in 1N NaOH (20 mL) was treated with a solution of N,N-dimethylsulfamyl chloride (2.3 mL) in THF (20 mL) and stirred vigorously at 25° C. for 3 hours. The reaction mixture was then treated with additional 1N NaOH (20 mL) and N,N-dimethylsulfamyl chloride (2.3 mL) and stirred 3 hours further at 25°. Finally 1N NaOH (20 mL) and diethyl ether (80 mL) were added. The mixture was shaken and the aqueous layer was separated and acidified to pH 1 by addition of 1N HCl (25 mL). The product was extracted into ethyl acetate, the solution dried over MgSO$_4$, and evaporated to give a gum which slowly solidified (4.0 g). The structure was confirmed by NMR spectroscopy.

B

SMO-PHE

Prepared as above, substituting morpholinosulfamyl chloride (prepared according to the method of R. Wegler and K. Bodenbenner, *Annallen der Chemie*, 624, 25 (1959)) for N,N-dimethylsulfamyl chloride. The product is a solid, mp 151–153° C.

C

DMSA-TYR(OME)

Prepared as above, substituting TYR(OMe) for PHE. The product was isolated as its dicyclohexylamine salt, mp 157–159° C.

D

DMSA-TYR(OME)

Prepared as above, substituting TYR(OME) for PHE. The structure was confirmed by NMR spectroscopy.

E

BOC-ATG(Z)

Prepared as in reference *J. Chem. Soc. Perkin Trans. I*, p 1227 (1984).

To a solution of ethyl 2-aminothiazol-4-ylacetate (27.4 g) in water (200 mL) was added K$_2$CO$_3$ until pH=9 (wet litmus). To this was added BOC$_2$O (26.0 g) in THF (150 mL) and the pH continually adjusted to 9 with K$_2$CO$_3$. The mix stirred for 24 hours. The basic solution was then extracted with ethyl acetate (2×400 mL). The organics were washed with brine (3090 mL) and dried over MgSO$_4$. Evaporation gave a brown oil which was recrystallized from ethyl acetate (100 mL) and petroleum ether (600 mL). This gave 23.5 g of a beige solid (ethyl-N-BOC-2-aminothiazol-4ylacetate). This ester (15.07 g) was then dissolved in a mixture of THF (65 mL), CH$_2$Cl$_2$ (100 mL) and saturated NaHCO$_3$ solution (700 mL). To this was added benzylchloroformate (21.3 g) and the mixture vigorously stirred for 18 hours. The solution was diluted with water (100 mL) and ethyl acetate (150 mL). The organics were separated, washed with water (2×400 mL), and evaporated at reduced pressure to give an oil which was dissolved in EtOH (150 mL) and treated with a solution of potassium hydroxide (14 g) in water (100 mL). The mixture was stirred for 1.5 hours and diluted with water (350 mL). The solution was washed with ether (2×250 mL) and the ethereal solution discarded. The aqueous solution was made acidic (pH=3, wet litmus) with citric acid and cooled to precipitate. Collection of the solid gave 16.8 g of product.

F

BOC-ATM(Z)

Prepared in a similar manner as BOC-ATG(Z) from ATM.2HCl which was prepared as in reference *Chem. Ber.*, Vol. 97, p 1767 (1964).

Sodium metal (0.64 g) was dissolved in ethanol (75 mL) and the solution treated with diethyl acetamido malonate (6.08 g) and stirred for 0.5 hours. This was then treated with 2-acetamidothiazol-4-yl-1-chloromethane (5.3 g) and sodium iodide (4.17 g). The mixture was stirred under nitrogen for 24 hours. The solution was filtered free of solids. The solids were triturated with water (150 mL). The mixture was again filtered to collect solid and washed with water (2×150 mL). This solid (2.75 g) was dissolved in concentrated hydrochloric acid (40 mL) and warmed to reflux for 3 hours.

The solution was evaporated in vacuo and co-evaporated with ethanol (2×50 mL). The resultant solid was triturated with ether (100 mL) and filtered to give 1.91 g of product as a white solid.

G

BOC-ATM(Z)-CAD

The compound was prepared as in Example 1 from BOC-ATM(Z) (6.3 g), HOBT (2.02 g), DCC (3.1 g), CAD.HCl (4.19 g) and Et$_3$N: (1.5 g). This gave 5.7 g of the product as a mixture of diastereomers as a white foam, mp 95–100° C. The structure was confirmed by NMR and mass spectroscopy.

H

ATM(Z)-CAD

The compound was prepared by saturating a solution of BOC-ATM(Z)-CAD (5.35 g) in CH$_2$Cl$_2$ (70 mL) and MeOH (10 mL) with HCl gas. The solution was stirred at room temperature for 2 hours and then evaporated in vacuo to dryness. The residue was dissolved in EtOAc (75 mL) and washed successively with saturated NaHCO$_3$ (2×100 mL) and saturated salt solution (100 mL). The organic phase was dried over MgSO$_4$ and evaporated in vacuo to give 3.8 g of product as a mixture of diastereomers as a light yellow foam, mp 84–91° C. The structure was confirmed by NMR and mass spectroscopy.

I

BOC-ATM(Z)-CST-AEM

The compound was synthesized as in Example 1 from BOC-ATM(Z) (4.21 g), HOBT (1.35 g), DCC (2.06 g) and CST-AEM (3.27 g). This gave 4.6 g of product as a mixture of diastereomers as a white foam, mp 97–100° C. The structure was confirmed by NMR and mass spectroscopy.

J

ATM(Z)-CST-AEM

The compound was prepared as in ATM(Z)-CAD from BOC-ATM(Z)-CST-AEM (4.4 g). This gave 3.78 g of product as a mixture of diastereomers as a white foam, mp 80–83° C. The structure was confirmed by NMR and mass spectroscopy.

K

BOC-ATM(Z)-STA-MBA

The compound was synthesized as in Example 1 from BOC-ATM(Z) (1.0 g), HOBT (0.338 g), DCC (0.516 g), and STA-MBA (0.733 g). This gave 1.25 g of product as a mixture of diastereomers as a white foam. The structure was confirmed by NMR and mass spectroscopy.

L

ATM(Z)-STA-MBA

The compound was synthesized as in ATM(Z)-CAD above from BOC-ATM(Z)-STA-MBA (1.25 g). This gave 0.9 g of product as a mixture of diastereomers as a light yellow foam. The structure was confirmed by NMR and mass spectroscopy.

M

BOC-ATG(Z)-STA-MBA

The compound was synthesized as in Example 1 from BOC-ATG(Z) (6.1 g), HOBT (2.16 g), DCC (3.3 g), and STA-MBA (3.7 g). This gave 8.8 g of product as a mixture of diastereomers as a white foam, mp 86–91° C. The structure was confirmed by NMR and mass spectroscopy.

N

ATG(Z)-STA-MBA

The compound was prepared as in ATM(Z)-CAD from BOC-ATG(Z)-STA-MBA (3.17 g). This gave 2.2 g of product as a mixture of diastereomers as a light yellow foam, mp 76–83° C. The structure was confirmed by NMR and mass spectroscopy.

O

BOC-(S)ATM-OBZL.HCL

N-BOC-Aspartatic acid, α-benzyl ester (40 g, 0.124 mol) in EtOAc (1L) was treated at 0° C. with N-methylmorpholine (13.8 g, 0.136 mol) and isobutyl chloroformate (18.6 g, 0.136 mol). The mixture was stirred at 0–10° C. for 3 hours. The mixture was filtered free of precipitate and treated with a solution of diazomethane [(~0.175 mol) freshly distilled from diazald (53 g)] in ether (~500 mL). The mixture was stirred for 16 hours under a N₂ stream. The solution was washed with saturated salt solution (500 mL) and evaporated in vacuo to give the diazoketone as a dark oil. This oil was dissolved in ether (400 mL) and carefully treated with HCl gas. The gas treatment stopped when the pH of the solution reached 2 (wet litmus), approximately two to 8 minutes. The solution was then immediately treated with a solution of saturated sodium bicarbonate (600 mL). The organics were washed with saturated salt solution (200 mL) and dried over MgSO₄. The organics were evaporated in vacuo to give 44.4 g of the chloroketone as a tan solid. This was dissolved in acetone (225 mL) and treated in portions with thiourea (7.6 g, 0.1 mol). The solution was stirred at room temperature for 24 hours. The mixture was filtered to collect solid, the solid washed with acetone (2×75 mL) and dried in vacuo to give 20.6 g of product as a white solid, mp=144–146° C. The structure was confirmed by NMR and mass spectroscopy.

P

BOC-(S)ATM(Z)

Prepared in a manner similar to BOC-ATM(Z) from BOC-(S)ATM-OBZL.HCl as in ref. *Chem. Ber.*, Vol. 97, p. 1767 (1964).

Q

BOC-(S)ATM(Z)-CAD

To BOC-(S)ATM(Z)-OBZL.HCl (2.06 g) in methanol (35 mL) was added a solution of NaOH (0.6 g) in water (10 mL). The solution was stirred at room temperature for 4 hours and then taken to pH=6 (wet litmus) with 1N HCl. The solution was evaporated in vacuo and dissolved in DMF (20 mL). This solution was treated at 0° C. sequentially with Et₃N (1.51 g), HOBT (0.667 g), DCC (1.03 g), and CAD (1.22 g). The mixture was stirred for 72 hours. The mixture was filtered free of solids and the solvent evaporated in vacuo. The residue from evaporation was dissolved in EtOAc (100 mL) and washed sequentially with saturated sodium bicarbonate (100 mL) and saturated salt solution. The organics were dried over MgSO₄ and evaporated in vacuo to give a yellow foam. The foam was chromatographed over silica gel to give the product as a white solid, 1.2 g. The structure was confirmed by NMR and mass spectroscopy.

R

(S)ATM(Z)-CAD.2HCl

To BOC-(S)ATM(Z)-CAD (1.1 g) in a mix of CH₂Cl₂ (75 mL) and MeOH (15 mL) was added HCl (gas) and the solution stirred at room temperature for 3 hours. The solution was evaporated in vacuo to give the product, which was used without further purification. The structure was confirmed by NMR and mass spectroscopy.

S

BOC-(S)ATE-OBZL

The compound was synthesized as in intermediate O BOC-(S)-ATM-OBZL from 42.2 g of N-BOC-GLU-OBZL 18.6 g i-butyl chloroformate, 13.8 g N-methyl morpholine, and excess Diazomethane. Silica gel chromatography gave 15.2 g of product. The structure was confirmed by NMR, IR and mass spectroscopy.

T

BOC-(S)ATE(Z)-OBZL

The compound was synthesized as in intermediate BOC-(S)ATM(Z)-OBZL from 14.17 g BOC-(S)ATE- OBZL, and 15.4 g Z-Cl. Extraction workup with EtOAc gave after evaporation 18.9 g of product. The structure was confirmed by NMR spectroscopy.

U

BOC-(S)ATE(Z)

A mixture of 18.9 g BOC-(S)-ATE(Z)-OBZL and 7 g NaOH were stirred in a mixture of 100 mL methanol and 20 mL water for 6 hours. The mixture was evaporated and treated with 100 mL 1N NaOH, then washed with 100 mL diethyl ether. The aqueous solution made acidic with 6N HCl and extracted with ethyl acetate (2×150 mL). Drying over $MgSO_4$ and evaporation gave 9.3 g of product. The structure was confirmed by spectroscopy.

V

BOC-(S)ATE(Z)-CAD

The compound was synthesized as in Example 1 from 9.3 g BOC-(S)ATE(Z), 2.7 g HOBT, 4.12 g DCC and 4.9 g CAD. Silica gel chromatography with ethyl acetate gave 7.6 g of product. The structure was confirmed by NMR and mass spectroscopy.

W

TROC-PIP.HCl

A solution of 2.37 mL $Cl_3CCH_2OCOCl$ (17.22 mmol) in 65 mL $CH_2Cl_2$ was added dropwise to a chilled solution of 15.00 g piperazine (174.13 mmol, a 10-fold excess) in 75 mL MeOH under $N_2$ atmosphere and allowed to stir at room temperature for 3 hours. The reaction mixture was diluted with MeOH and evaporated to a wet solid. The residue was taken up in $H_2O$ and extracted with EtOAc. The organic layer was dried over $MgSO_4$ and evaporated. The resulting oil was dissolved in 40 mL $Et_2O$ and treated dropwise with a 1.0M HCl solution in 40 mL $Et_2O$ under $N_2$ atmosphere to give 2.45 g of the product as a white solid. mp 209–213° C.

X

TROC-SPI-Cl

A solution of 9.75 g TROC-PIP hydrochloride (32.72 mmol) in 20 mL $H_2O$ was mixed with 40 mL $CH_2Cl_2$ and was cooled in ice, treated dropwise by a solution of 48.60 g 5.25% NaOCl (34.03 mmol) in $H_2O$ and stirred on ice for 50 minutes. The organic layer was separated and dried over $MgSO_4$. The resulting solution was added to a −78° solution of 30.00 g $SO_2$ in 20 mL $CH_2Cl_2$, and catalytic amount of $Cl_2$ (6 drops) was condensed into the reaction mixture under $N_2$ atmosphere. The reaction mixture was allowed to warm up to room temperature over 24 hours. The solvent was evaporated, and the residue was partitioned between $CH_2Cl_2$ and 0.25M $K_2PO_4$, pH=7 buffer and washed with 10% $Na_2S_2O_3$. The organic layer was dried over $MgSO_4$ and evaporated to give 8.02 g of the product as a golden brown solid. The structure was confirmed by NMR spectroscopy.

Y

BOC-ATG(Z)-CAD

A solution of 2.2 g (8 mmol) of CAD-hydrochloride, 1 g (10 mmol) of $Et_3N$, 1.1 g (8 mmol) of HOBT, and 3.3 g (8 mmol) BOC-ATG(Z) in 45 mL of DMF was cooled in ice and treated with 1.7 g (8 mmol) of DCC in 10 mL of DMF. After 0.5 hour at 0° C., the mixture was allowed to stir at room temperature for 48 hours. DMF was distilled and the residue was treated with EtOAc. The urea was filtered off and the residue was washed with additional quantities of EtOAc. The filtrate and the washings were combined, and washed successively with water, saturated $NaHCO_3$, and brine. Drying and removal of the solvent under reduced pressure gave the crude product. This was purified via chromatography ($SiO_2$, $CH_2Cl_2/CH_3OH$ 10%) to give 6 g of product. The structure was confirmed by NMR spectroscopy.

Z

ATG(Z)-CAD.HCl

A solution of 6 g of BOC-ATG(Z)-CAD in 60 mL of $CH_2Cl_2$ was saturated with HCl (g), and allowed to stand at room temperature for 2 hours. The solution was evaporated to give a foam. The structure was confirmed by $^1H$ NMR and mass spectrum (M+1 peak at 533). This material was used as is for coupling.

AA

BOC-(S)ATM(TROC)-FCS-AEM

To BOC-(S)ATM(TROC) (2.60 g, 5.63 mmol) and HOBt (0.76 g, 5.63 mmol) in anhydrous DMF (30 mL) at 0° C. was added DCC (1.16 g, 5.63 mmol) in DMF (10 mL) followed by FCS-AEM (2.04 g, 5.63 mmol) in DMF (10 mL) and the reaction stirred at 0° C. for 2 hours before warming to room temperature. After 16 hours the reaction was filtered and the solvent evaporated under reduced pressure. The residue was taken up in ethyl acetate (50 mL) and washed with saturated aqueous sodium bicarbonate solution, water, and brine, respectively. After drying ($Na_2SO_4$), the solvent was evaporated and the crude material chromatographed on silica gel eluting with a gradient of 3 to >5% methanol in $CH_2Cl_2$. The product was obtained as a white foam (3.0 g, 66%) and the structure confirmed by NMR and mass spectroscopy; MS(FAB):MH+ 807.2.

BB

(S)ATM(TROC)-FCS-AEM

BOC-(S)ATM(TROC)-FCS-AEM (2.20 g, 0.27 mmol), in a mixture of $CH_2Cl_2$ (30 mL) and methanol (10 mL) was subjected to a stream of HCl gas at room temperature for 15 minutes. After stirring for a further 20 minutes, the solvent was evaporated and the residue taken up in chloroform and reevaporated. This procedure was repeated twice more before addition of ethyl acetate to the crude product. The solution was washed with saturated aqueous bicarbonate solution to generate the free base. The aqueous layer was separated and extracted twice with ethyl acetate. The combined organic extracts were washed with brine and dried ($Na_2SO_4$). After evaporation of the solvent the free amine was obtained as a white foam (1.90 g, 99%). The structure was confirmed by NMR and mass spectroscopy; MS(FAB) M+ 707.0.

CC

BOC-FCS-AEM

To BOC-FCS (4.10 g, 12.0 mmol) and HOBt (1.58 g, 12.0 mmol) in DMF (100 mL) at 0° C. was added DCC (2.41 g, 12.0 mmol) in DMF (20 mL). After 5 minutes, AEM (1.53 mL) in DMF (10 μL) was added and the reaction stirred for 2 hours before warming to room temperature and stirring for a further 16 hours. The mixture was filtered and the solvent evaporated under high vacuum. The residue was taken up in ethyl acetate and washed with saturated sodium bicarbonate solution, water, and brine respectively. After drying ($Na_2SO_4$) the solvent was evaporated and the crude product purified by column chromatography on silica gel eluting with 5% to 7% methanol in dichloromethane. The product was obtained as a white foam (3.38 g, 63%) and the structure confirmed by NMR and mass spectroscopy:MS(FAB) MH+(464).

DD

BOC-(S)ATM(TROC)-OBZL

A solution of 9.56 g (25 mmol) BOC-(S)ATM-OBZL was suspended in $CH_2Cl_2$ and cooled in an acetone/ice bath. Added to this was 7.74 g DMAP (2.5 equivalent); goes into solution. TROC-Cl of 8.40 mL (12.34 g, 2.3 equivalent) was added dropwise. After 4 hours the solution is washed sequentially with water, 0.1N HCl, saturated aqueous NaCl, and dried ($MgSO_4$), then concentrated. The residue is chromatographed (400 g $SiO_2$, eluting 1:1 hexane/ethyl acetate. The product was isolated as a colorless foam, 12.80 g. Mass spectrum m/e=552

EE

BOC-(S)ATM(TROC)

BOC-(S)ATM(TROC)-OBZL of 3.60 g (17.6 mmol) was dissolved in 100 mL methanol at room temperature. KOH (1.16 g) (85%, 2.7 equivalent) was dissolved in 10 mL water and added to the solution. Stir for 3.5 hours. An additional 50 mL of water was added, the reaction partially concentrated, then extracted with EtOAc. These organics were discarded. The aqueous solution was then rendered acidic (6N HCl, forms precipitate), and extracted again with EtOAc. These organics were washed with saturated aqueous NaCl, dried ($MgSO_4$) and concentrated to give 2.54 g product as a waxy white solid. Mass spectrum m/e=462

FF

BOC-(S)ATM(TROC)-CAD

BOC-(S)ATM(TROC) 27.25 g (58.9 mmol) was dissolved in EtOAc and cooled in ice bath. CAD (14.33 g, 58.9 mmol) was added, resulting in a suspension. To this was added 7.98 g HOBT and 12.13 g DCC (one equivalent each), and the reaction mixture allowed to come to ambient temperature overnight. The reaction was filtered, and the filtrate washed sequentially with 5% aqueous citric acid, saturated $NaHCO_3$, saturated NACl, then dried ($MgSO_4$) and concentrated to afford 31.0 g product. This was recrystallized in 150 mL boiling EtOAc. The first crop yielded 20.50 g, and a second crop 2.43 g product. An additional 6.59 g product was recovered by washing the original filter cake with acetone and concentrating this filtrate. Mass spectrum m/e=689

GG

BOC-(S)ATM(TROC)-CDH

BOC-(S)ATM(TROC) (2.50 g, 5.4 mmol) was dissolved in methylene chloride and the solution cooled in an ice bath. CDH (1.25 g, 0.95 equivalent) was added, followed by 0.70 g HOBT, 1.06 g DCC, and 1.26 g DMAP. The mixture was allowed to come to ambient temperature overnight, then filtered and the filtrate washed sequentially with 1N HCl, saturated $NaHCO_3$, saturated NaCl, and dried ($MgSO_4$). After concentration, the residue was chromatographed ($SiO_2$, EtOAc) to give 0.76 g product. This was used without further purification in the next reaction.

HH

SMO-PHE-(S)ATM(Z)

SMO-PHE-(S)ATM(Z)-OBZL (5.6 g) and 0.64 g NaOH were stirred in a mix of 70 mL methanol and 15 mL water for 5 hours. The mixture was evaporated in vacuo and the residue partitioned between 100 mL EtOAc and 100 mL 2N HCl. The organics were separated and dried over $MgSO_4$. Evaporation of solvents gave 4.5 g of product.

II

(S)ATM(Z)-OBZL.HCl

BOC-(S)ATM(Z)-OBZL (10.8 g) was dissolved in 8 mL MeOH and 50 mL $CH_2Cl_2$ and treated with HCl(g) at room temperature for 3 hours. Evaporation gives 8.8 g of product as the HCl salt. The structure was confirmed by NMR, IR, and mass spectroscopy.

JJ

SMO-PHE-(S)ATM(Z)-OBZL

The compound was synthesized as in Example 1 from 3.14 g SMO-PHE, 1.35 g HOBT, 2.06 g DCC, 2.02 g $Et_3N$ and 4.3 g (S)ATM(Z)-OBZL. Chromatography on the Waters prep 500A using 5% methanol/$CH_2Cl_2$ gave the product as a yellow solid, used as is.

KK

TROC-SPI-PHE

To a suspension of 5.09 g PHE (30.81 mmol) in 20 mL MeOH was added 12.97 mL of 5% $Me_4NOH$/MeOH (30.81 mmol) and the mixture stirred until a solution was obtained. The mixture was diluted with toluene and evaporated to a foam and dried at 0.05 mm at room temperature for 2 hours. To a suspension of the foam in 30 mL dry THF was added 60 mL dry i-PrOH and 5.49 g TROC-SPI-Cl. The mixture was allowed to stir at room temperature under $N_2$ atmosphere for 16 hours. The solvent was evaporated, and the residue was partitioned between $CH_2Cl_2$ and 1N HCl and washed with 1N HCl. The product was extracted from the organic layer into 0.3N NaOH which was immediately acidified to pH=1 with concentrated HCl and reextracted with EtOAc. The EtOAc layers were washed with 1N HCl, saturated NaCl, dried over $MgSO_4$ and evaporated to obtain 3.59 g of the product as a golden brown solid. The structure was confirmed by NMR spectroscopy.

LL

FCS-AEM

To BOC-FCS-AEM (5.17 g) in dry $CH_2Cl_2$ (100 mL) was added 6 mL of TFA at RT and the reaction stirred for 6 hours. After concentration the residue was treated with saturated $NaHCO_3$ solution and the product extracted into ethyl acetate and washed with brine and dried ($Na_2SO_4$). Dried under high vacuum for several hours to give the product as a white foam, 3.65 g. Compound confirmed by NMR spectroscopy.

MM

BOC-(S)ATM(Z)-CYSTA-BHEAEA

The product was prepared as in Example 1 from BOC-(S)ATM(Z) (5 g), HOBT (1.68 g), DCC (2.6 g) and CST-BHEAEA (4.1 g) in DMF (25 mL). This gave 3.26 g of product after silica gel chromatography (19:1, CH$_2$Cl$_2$:MeOH).

Analyzed for C$_{36}$H$_{56}$N$_6$O$_9$S.0.8CHCl$_3$:
Calc'd: C, 52.34; H, 6.78; N, 9.95.
Found: C, 52.52; H, 6.91; N 9.91.

NN

BOC-FCS-OET

To a suspension of Zn dust (15.3 g) in THF (300 mL) was added one crystal of I$_2$ and the mixture brought to reflux. To this was added sequentially bromodifluoro ethyl acetate (0.2 mL) followed by a mixture of the same ester (25.3 g) and (S)-BOC-cyclohexyl alanol (20 g) in THF (100 mL). The mixture was filtered free of insoluble material and the solvents evaporated at reduced pressure. The residue was dissolved in ethyl acetate and the pH adjusted with 1M KHSO$_4$ solution until pH=2. This solution was filtered free of solids and the organics separated from the filtrate. The aqueous solution was extracted with ethyl acetate (2×) and the combined organic layers washed with brine, dried over magnesium sulfate, and evaporated in vacuo to give a yellow solid. The solid was triturated with 20% ethyl acetate in hexane to give the product as a white solid, 6.5 g. NMR and IR were consistent with the structure.

OO

FCS-OET.HCl

To BOC-FCS-OET (5.3 g) in methanol (250 mL) was added HCl gas, gas dispersion tube, until the solution was saturated. The solution was stirred at room temperature for 2 hours and evaporated at reduced pressure to give the product as a white solid, 4.5 g. NMR was consistent with structure.

PP

BOC-(S)ATM(TROC)-FCS-OET

The compound was synthesized as in Example 1 from BOC-(S)ATM(TROC) (5.90 g), HOBT (1.73 g), DCC (2.64 g), Et$_3$N (1.43 mL), and FCS-OET.HCl (4.03 g). This gave, after silica gel chromatography (4% MeOH/CH$_2$Cl$_2$) 2.55 g of product. NMR spectra were consistent with the structure.

QQ

(S)ATM(TROC)-FCS-OET

To BOC-(S)ATM(TROC)-FCS-OET (2.54 g) in EtOH (25 mL) was added CH$_2$Cl$_2$ (200 mL) and the solution saturated with HCl gas. The mixture was allowed to stand overnight and then evaporated at reduced pressure. This solid was partitioned between EtOAc (250 mL) and saturated NaHCO$_3$ solution (200 mL). The organic phase was washed with brine and dried over MgSO$_4$. Evaporation of solvents gave 1.97 g of product.

Analysis
Calc'd: C, 40.01; H, 4.88; N, 8.48.
Found: C, 38.03; H, 4.94; N, 8.50.

RR and SS

BOC-ATG(Z)-FCS-AEM (Isomer A) RR
BOC-ATG(Z)-FCS-AEM (Isomer B) SS

The compounds were synthesized as in Example 1 from BOC-ATG(Z) (3.3 g), HOBT (1.1 g, DCC (1.7 g), and FCS-AEM (2.9 g). This gave after silica gel chromatography (3–5% MeOH/CH$_2$Cl$_2$), 1.9 g of isomer A (fast eluting) and 1.9 g of isomer B (slow eluting). Both compounds gave NMR, IR, and mass spectra consistent with structures.

TT

ATG(Z)-FCS-AEM, Isomer A

The compound was synthesized as in intermediate H, from BOC-ATG(Z)-FCS-AEM, Isomer A (1.9 g). This gave 1.5 g of free base which was used as is.

UU

ATG(Z)-FCS-AEM, Isomer B

The compound was synthesized as in intermediate H, from BOC-ATG(Z)-FCS-AEM, Isomer B (1.9 g). This gave 1.7 g of free base which was used as is.

We claim:

1. A method of treating renin-associated hypertension which comprises administering to a mammal a pharmaceutical composition comprising a renin-inhibitory effective amount of a compound of the formula

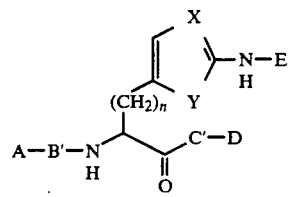

or a pharmaceutically acceptable acid addition salt thereof wherein

A is 2-Benzyl-3-(t-butylsulfonyl)propionyl (BBSP),

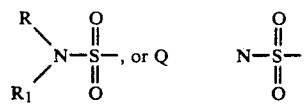

wherein R and R$_1$ are each independently hydrogen or straight or branched chain lower alkyl which is unsubstituted or substituted by one or two hydroxy, one or two amino groups, or

wherein

is a saturated ring containing two to five carbon atoms wherein Q is CH$_2$, O, S, or NR wherein R is as above, only one

ring can be present at one time;

B' is absent, PHE, or TYR(OME) with the proviso that when A is BBSP, B' is absent;

C' is

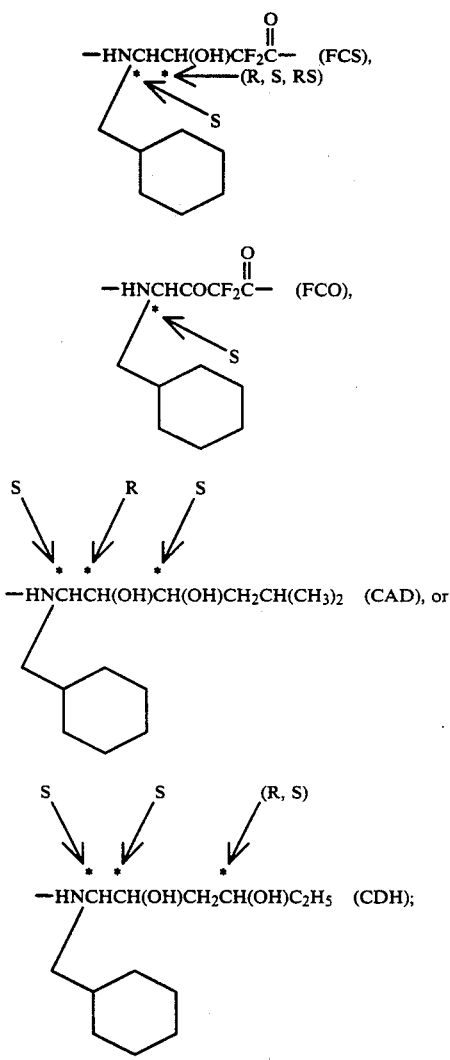

D is absent, or NR$_2$R$_3$ wherein R$_2$ and R$_3$ are each independently hydrogen or straight or branched lower alkyl or when R$_2$ is hydrogen, R$_3$ can also be —(CH$_2$)$_m$X' wherein m is an integer of from zero to eight and X' is

as defined above, NR$_5$R$_6$ wherein R$_5$ and R$_6$ are each independently hydrogen, straight or branched chain lower alkyl substituted or unsubstituted by one or two hydroxy or amino groups with the proviso that when C' is CAD, D is absent;

E is hydrogen;

n is an integer from 0 to 2;

X and Y are each independently O, S, N or NH and at least one of X and Y must be N; X and Y cannot both be N together with a pharmaceutically acceptable carrier.

2. A method of treating hyperaldosteronism which comprises administering to a mammal a pharmaceutical composition comprising a hyperaldosteronism inhibitory effective amount of a compound of the formula

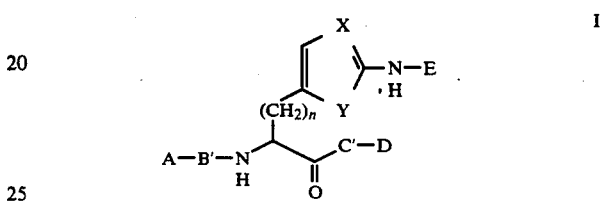

or a pharmaceutically acceptable acid addition salt thereof wherein

A is 2-Benzyl-3-(t-butylsulfonyl)propionyl (BBSP),

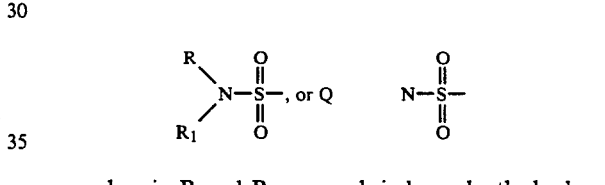

wherein R and R$_1$ are each independently hydrogen or straight or branched chain lower alkyl which is unsubstituted or substituted by one or two hydroxy, one or two amino groups, or

wherein

is a saturated ring containing two to five carbon atoms wherein Q is CH$_2$, O, S, or NR wherein R is as above, only one

ring can be present at one time;

B' is absent, PHE, or TYR(OME) with the proviso that when A is BBSP, B' is absent;

C' is

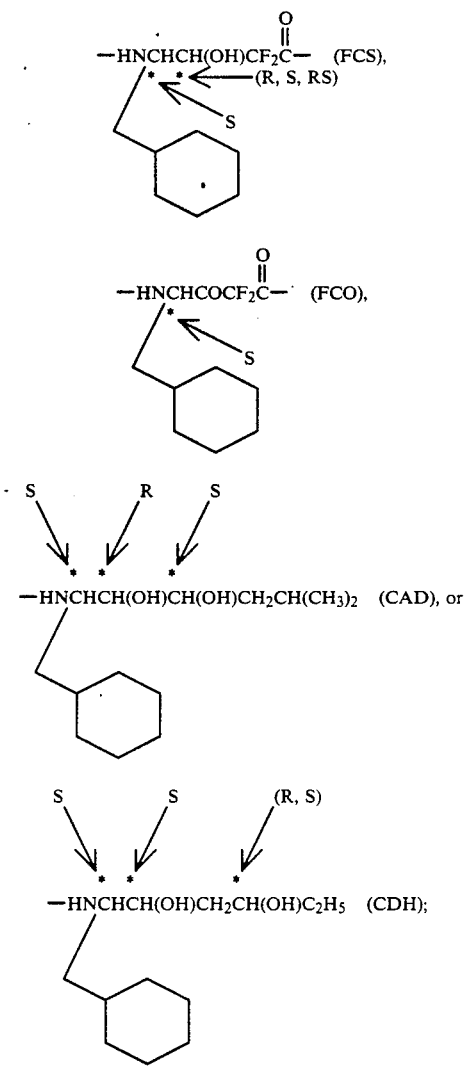

D is absent, or NR$_2$R$_3$ wherein R$_2$ and R$_3$ are each independently hydrogen or straight or branched lower alkyl or when R$_2$ is hydrogen, R$_3$ can also be —(CH$_2$)$_m$X' wherein m is an integer of from zero to eight and X' is

as defined above, NR$_5$R$_6$ wherein R$_5$ and R$_6$ are each independently hydrogen, straight or branched chain lower alkyl substituted or unsubstituted by one or two hydroxy or amino groups with the proviso that when C' is CAD, D is absent;

E is hydrogen;

n is an integer from 0 to 2;

X and Y are each independently O, S, N or NH and at least one of X and Y must be N; X and Y cannot both be N together with a pharmaceutically acceptable carrier.

3. A method of treating congestive heart failure which comprises administering to a mammal a pharmaceutical composition comprising an amount effective for treating congestive heart failure of a compound of the formula

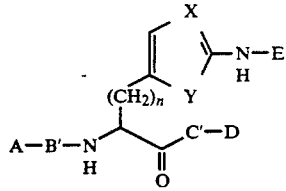

or a pharmaceutically acceptable acid addition salt thereof wherein

A is 2-Benzyl-3-(t-butylsulfonyl)propionyl (BBSP),

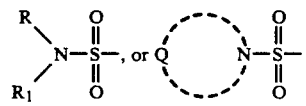

wherein R and R$_1$ are each independently hydrogen or straight or branched chain lower alkyl which is unsubstituted or substituted by one or two hydroxy, one or two amino groups, or

wherein

is a saturated ring containing two to five carbon atoms wherein Q is CH$_2$, O, S, or NR wherein R is as above, only one

ring can be present at one time;

B' is absent, PHE, or TYR(OME) with the proviso that when A is BBSP, B' is absent;

C' is

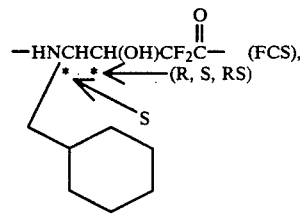

-continued

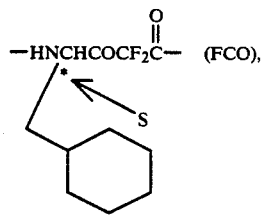
—HNCHCOCF₂C—  (FCO),

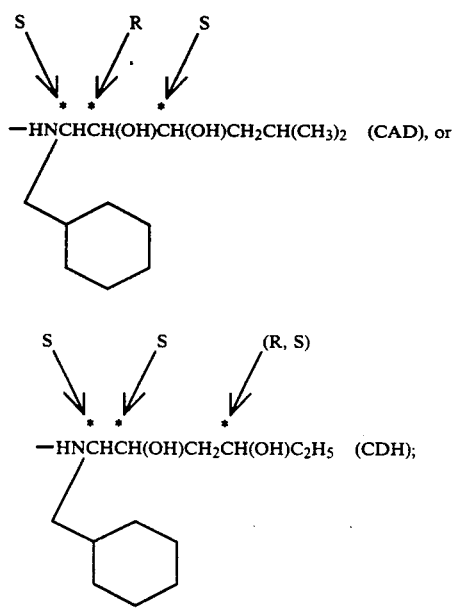
—HNCHCH(OH)CH(OH)CH₂CH(CH₃)₂  (CAD), or

—HNCHCH(OH)CH₂CH(OH)C₂H₅  (CDH);

D is absent, or NR₂R₃ wherein R₂ and R₃ are each independently hydrogen or straight or branched lower alkyl or when R₂ is hydrogen, R₃ can also be —(CH₂)ₘX' wherein m is an integer of from zero to eight and X' is

as defined above, NR₅R₆ wherein R₅ and R₆ are each independently hydrogen, straight or branched chain lower alkyl substituted or unsubstituted by one or two hydroxy or amino groups with the proviso that when C' is CAD, D is absent;

E is hydrogen;

n is an integer from 0 to 2;

X and Y are each independently O, S, N or NH and at least one of X and Y must be N; X and Y cannot both be N together with a pharmaceutically acceptable carrier.

4. A method of determining the presence of renin-associated hypertension in a patient, comprising administering to such a patient, at a hypotensive dosage level and as a single dose, a compound of the formula

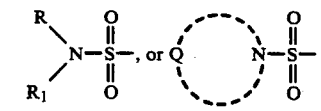

or a pharmaceutically acceptable acid addition salt thereof wherein

A is 2-Benzyl-3-(t-butylsulfonyl)propionyl (BBSP),

wherein R and R₁ are each independently hydrogen or straight or branched chain lower alkyl which is unsubstituted or substituted by one or two hydroxy, one or two amino groups, or

wherein or

is a saturated ring containing two to five carbon atoms wherein Q is CH₂, O, S, or NR wherein R is as above, only one

ring can be present at one time;

B' is absent, PHE, or TYR(OME) with the proviso that when A is BBSP, B' is absent;

C' is

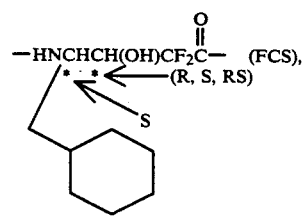
—HNCHCH(OH)CF₂C—  (FCS),
(R, S, RS)

-continued

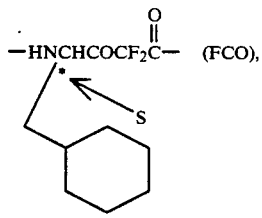
(FCO),

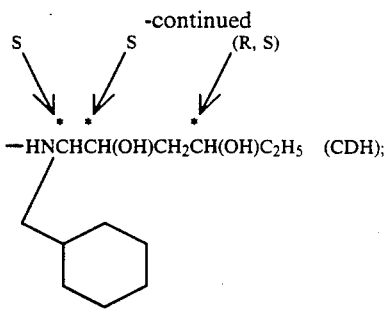
(CDH);

D is absent, or NR₂R₃ wherein R₂ and R₃ are each independently hydrogen or straight or branched lower alkyl or when R₂ is hydrogen, R₃ can also be —(CH₂)$_m$X' wherein m is an integer of from zero to eight and X' is

as defined above, NR₅R₆ wherein R₅ and R₆ are each independently hydrogen, straight or branched chain lower alkyl substituted or unsubstituted by one or two hydroxy or amino groups with the proviso that when C' is CAD, D is absent;

E is hydrogen;

n is an integer from 0 to 2;

X and Y are each independently O, S, N or NH and at least one of X and Y must be N; X and Y cannot both be N together with a pharmaceutically acceptable carrier followed by monitoring of said patient's blood pressure.

* * * * *

UNITED STATES PATENT AND TRADEMARK OFFICE
CERTIFICATE OF CORRECTION

PATENT NO. : 5,238,923
DATED : August 24, 1993
INVENTOR(S) : Connolly, et al

It is certified that error appears in the above-indentified patent and that said Letters Patent is hereby corrected as shown below:

Column 32, lines 46-49, structure should appear as:

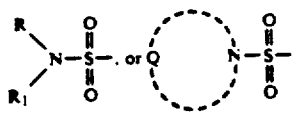

Column 34, lines 32-35, structure should appear as:

Signed and Sealed this

Fifth Day of July, 1994

*Attest:*

BRUCE LEHMAN

*Attesting Officer*     *Commissioner of Patents and Trademarks*